United States Patent [19]

Saito et al.

[11] Patent Number: 4,963,687

[45] Date of Patent: Oct. 16, 1990

[54] PROCESS FOR PRODUCING CYANOPYRIDINES

[75] Inventors: Masao Saito, Tokyo; Kengo Tsukahara, Niigata; Koichiro Yamada, Niigata; Hisasi Imai, Niigata, all of Japan

[73] Assignee: Mitsubishi Gas Chemical Company, Inc., Tokyo, Japan

[21] Appl. No.: 341,874

[22] Filed: Apr. 24, 1989

[30] Foreign Application Priority Data

Apr. 28, 1988 [JP] Japan .................................. 63-103766

[51] Int. Cl.$^5$ ............................................ C07D 213/57
[52] U.S. Cl. ............................................................ 546/286
[58] Field of Search ............................ 546/286; 502/202

[56] References Cited

U.S. PATENT DOCUMENTS

| | | | |
|---|---|---|---|
| 3,868,400 | 2/1975 | Norton | 546/286 |
| 3,959,297 | 5/1976 | Ishioka et al. | 546/286 |
| 3,959,339 | 5/1976 | Saito et al. | 546/286 |
| 3,970,657 | 7/1976 | Elion et al. | 546/286 |
| 4,057,552 | 11/1977 | Richtzenhain et al. | 546/258 |
| 4,447,612 | 5/1984 | Beschke et al. | 546/286 |

FOREIGN PATENT DOCUMENTS 0728664 2/1966 Canada .
1152878 12/1966 United Kingdom .

*Primary Examiner*—John M. Ford
*Attorney, Agent, or Firm*—Browdy and Neimark

[57] ABSTRACT

A process for producing a cyanopyridine which comprises reacting the corresponding methylpyridine, ammonia and an oxygen-containing gas in the presence of a catalyst comprising a vanadium oxide, a chromium oxide, a boron oxide and optionally a phosphorus oxide and/or molybdenum oxide held on silica is disclosed. According to the present invention, the reactivity of the raw material and the yield of the reaction product are high.

5 Claims, No Drawings

PROCESS FOR PRODUCING CYANOPYRIDINES

BACKGROUND OF THE INVENTION

This invention relates to a process for producing a cyanopyridine from the corresponding methylpyridine.

4-Cyanopyridine can be used as a medicine for tuberculosis.

3-Cyanopyridine can be used as a raw material for producing nicotinic acid amide which is used in medicines, feed additives, food additives or the like as one form of vitamin $B_1$.

PRIOR ARTS

Prior art processes for producing cyanopyridines have been proposed in the past.

U.S. Pat. No. 4,057,552 discloses a process for producing a cyanopyridine which comprises contacting an alkylpiperidine with ammonia in the presence of oxidized vanadium and in the absence of a gaseous oxygen. U.S. Pat. No. 3,959,297 discloses a process for producing 3-cyanopyridine which comprises reacting 2-methyl-5-ethylpyridine with ammonia in the presence of a catalyst comprising vanadium and zirconium as active components while introducing into the reaction system water in an amount of 20-80% by volume.

U.S. Pat. No. 4,447,612 discloses a process for producing 3-cyanopyridine which comprises reacting 3-methylpyridine, ammonia and oxygen in the presence of a catalyst comprising antimony, vanadium and at least one of iron, copper, titanium, cobalt, manganese and nickel.

The process disclosed in U.S. Pat. No. 4,057,552 uses a fluidized reactor. Some of the spent catalyst is withdrawn from the reactor, and volatile components are removed from the catalyst by stripping. The spent catalyst is oxidized by molecular oxygen in a regenerator; and the regenerated catalyst is recirculated into the reactor. This operation is complicated. The selectivity to 3-cyanopyridine in this process is as low as 15%.

Yields from the process disclosed in U.S. Pat. No. 3,959,297 are as high as 60%. A large volume of steam must be used to prevent the formation of 2,5-dicyanopyridine as a by-product in this process.

Though the yields obtained in the process disclosed in U.S. Pat. No. 4,447,612 are as high as 80-90%, a large volume of steam must be used to remove reaction heat in this process.

As mentioned above, some prior art processes have poor selectivity or poor yields, some require complicated operations, and some require a large volume of steam.

SUMMARY OF THE INVENTION

The present inventors have discovered a process for producing a cyanopyridine in high yield without the need for a complicated operation or for the introduction of a large volume of steam into the reaction system.

This invention relates to a process for producing a cyanopyridine which comprises reacting the corresponding methylpyridine, ammonia and an oxygen-containing gas in the presence of a catalyst comprising a vanadium oxide, a chromium oxide, a boron oxide and optionally a phosphorus oxide and/or molybdenum oxide held on silica.

DETAILED DESCRIPTION OF THE INVENTION

The atomic ratio of the vanadium, chromium, boron and phosphorus is preferably 1:0.5 to 2:0.1 to 1.2:0 to 0.3. And atomic ratio of vanadium, chromium, molybdenum and boron is preferably 1:0.5 to 2.0:0.01 to 1.2:0.01 to 1.2.

A vanadium oxide, a chromium oxide, a boron oxide, a phosphorus oxide and a molybdenum oxide can be used as they are as components constituting the catalyst of the present invention.

Vanadium compounds, such as ammonium metavanadate and vanadyl sulfate, and organic acid salts of vanadium, such as vanadium oxalate and vanadium tartrate, can be used instead of vanadium oxides. Chromium compounds, such as chromic acid, chromium nitrate, chromium hydroxide, ammonium chromate and ammonium bichromate, and organic acid salts of chromium, such as chromium oxalate and chromium tartrate, can be used instead of chromium oxides. Boron compounds, such as boric acid and ammonium borate, can be used instead of boron oxides. Phosphorus compounds, such as phosphoric acid and ammonium phosphate, can be used instead of phosphorus oxides. Molybdenum compounds, such as ammonium molybdate, ammonium paramolybdate, molybdic acid, molybdenum chloride and molybdenum salts of organic acids such as oxalic acid and tartaric acid, can be used instead of molybdenum oxide. When a vanadium compound, a chromium compound, a boron compound and/or a phosphorus compound are used, they are subjected to oxidation by heating during the preparation of a catalytic composition.

The catalysts of the present invention can be prepared by known methods. For example, an aqueous solution of boric acid and optionally an aqueous solution of phosphoric acid or aqueous ammonium molybdate solution may be added to a solution of vanadium oxide and chromic acid in oxalic acid. Then silica sol is added to the mixture to form a slurry. If necessary, a solubilizer for boric acid may be added to the mixture. Examples of suitable solubilizers include polyhydric alcohols, monooxy carboxylic acid and dioxycarboxylic acid. When fluidized bed catalysts are prepared, the mixtures are spray-dried and then calcined. When fixed bed catalysts are prepared, the liquid components are evaporated from the mixture and then the resulting solid materials are calcined. The calcination can be carried out at a temperature of 400°-700° C., preferably 450°-650° C., while air is passed through the mixture for a period of more than several hours.

If 2-methylpyridine, 3-methylpyridine or 4-methylpyridine is used, the corresponding cyanopyridine can be produced.

The concentration of methylpyridine in the reaction gas may be in the range of 0.5-5% by volume when using air as the oxygen-containing gas.

The ammonia in the raw gaseous mixture is used in a concentration beyond the theoretical amount. The higher the concentration of ammonia, the better the yield of the product is. However, when a large amount of ammonia is used, it is necessary to recover unreacted ammonia. Preferably, the amount of ammonia used is 2-10 times the theoretical amount.

Oxygen in the raw gaseous mixture is used in a concentration of at least 1.5 times the theoretical amount. Preferably, oxygen in an amount of 2-50 times the theoretical amount is used. Usually, air is used as the oxygen-containing gas. Air diluted with an inert diluent, such as nitrogen, carbon dioxide or steam may be used.

The reaction temperature may be in the range of 300°–500° C., preferably 330°–470° C. If the reaction temperature is lower than 300° C., the conversion of the methylpyridine is lowered. If the reaction temperature is higher than 500° C., the formation of carbon dioxide, hydrogen cyanide and the like increases, and the yield of cyanopyridine is therefore lowered. The appropriate reaction temperature for achieving the maximum yield depends upon the specific kind of cyanopyridine employed, the concentration of it and the length of time of the contact between the reaction gas and the catalyst.

The time of contact between the reaction gas and the catalyst may vary widely. The contacting time is usually in the range of 0.5–30 seconds.

The release of heat from the present reaction is great. It is therefore important to remove the heat of reaction. Through a fixed bed catalyst can be used to keep the temperature of catalyst bed at a suitable value, a fluidized bed catalyst or moving bed catalyst is more effective means of removing the heat of reaction. The present catalyst has excellent attrition resistance and fluidizability as a fluidized bed catalyst.

The present reaction is usually carried out at an atmospheric pressure. The reaction may be carried out in a pressurized manner or at a reduced pressure.

Recovery of the reaction product from the reaction mixture gas may be carried out by adopting suitable methods. For example, the reaction mixture gas may be cooled at such a temperature that the reaction product is solidified. The reaction mixture gas may be washed with water or a suitable solvent to recover the reaction product.

This invention is further explained by way of the following non-limiting examples. All percentages are on a weight basis, unless specified otherwise.

EXAMPLE 1

Oxalic acid $(COOH)_2 2H_2O$ (6.18 Kg) was added to water (5 l) heated at 80°–90° C. on a water bath, and dissolved therein. Vanadium pentaoxide ($V_2O_5$) (2.47 Kg) was gradually added to the mixture with stirring to form a solution of vanadium oxalate.

Oxalic acid (10.18 Kg) was added to water (9 l). Chromium trioxide (2720 g) was gradually added to the mixture with stirring while heating the mixture on a water bath to form a solution of chromium oxalate.

Boric acid (839 g) was added to water (50 l) and dissolved in the water by heating the mixture to 60°–70° C. to form a solution of boric acid.

Three these solutions were mixed to form a solution containing vanadium, chromium and boron. A 30% aqueous solution (16.70 Kg) of low alkaline silica sol was added to the solution containing vanadium, chromium and boron. The resulting mixture was violently stirred, and spray-dried at an inlet gas temperature of 250°. C. and an outlet gas temperature of 130° C. The resulting spray-dried material was treated at 250° C. for 12 hours in a calcinating furnace and calcined at 550° C. for 8 hours in a roasting furnace. The particle size of the resulting catalyst was 20–200 μm. The average particle size of the catalyst was 70 μm. The bulk density of the catalyst was 1.05 g/ml. The catalyst had attrition resistance of 0.15% by weight per hour, as measured by the ACC method. The atomic ratio of vanadium, chromium and boron in the resulting catalyst was 1:1:0.5. The amount of catalyst held on silica was 50%.

A portion of the catalyst (6 l) was charged into a stainless steel reactor having an inside diameter of 80 mm and heated by molten salt. A gaseous mixture of 3.0% by volume of 3-methylpyridine, 12.0% by volume of ammonia and 85% by volume of air was passed through the fluidized bed catalyst at 390° C. and SV of 600 hour$^{-1}$. Gas chromatograph analysis showed that the conversion of 3-methylpyridine was 93% and that the yield of 3-cyanopyridine was 90.5%.

EXAMPLE 2

A gaseous mixture of 3.0% by volume of 4-methylpyridine, 10.5% by volume of ammonia and 86.5% by volume of air was passed through the catalyst of Example 1 at 360° C. and SV of 600 hour$^{-1}$ by using the reactor of Example 1. The gas chromatograph analysis showed that the conversion of 4-methylpyridine was 99% and that the yield of 4-cyanopyridine was 92%.

EXAMPLE 3

Oxalic acid (618 g) was added to water (1000 ml). Vanadium pentaoxide (247 g) was added to the mixture while heating it at 80°–90° C. so that it dissolved in the water.

Anhydrous chromic acid (271.5 g) was dissolved in water (500 ml). The resulting solution was added to a slurry of oxalic acid (1048 g) dissolved in water (1500 ml) which had been heated to 50°–60° C. The resulting solution of vanadium oxalate and the resulting solution of chromium oxalate were mixed. The mixed solution was heat-concentrated so that the total amount of the solution amounted to 1500 ml. Boric acid (81 g), tartaric acid (200 g) and an 85% phosphoric acid solution (4.7 g) were added to the solution of vanadium oxalate and chromium oxalate to form a catalytic solution. The mixture was violently stirred. A 30% aqueous silica sol (1667 g) was added to the catalytic solution. The mixture was spray-dried at an inlet air temperature of 250° C. and an outlet gas temperature of 150° C. The resulting spray-dried material was treated at 250° C. for 12 hours in a calcinating furnace and calcined at 550° C. for 12 hours in a roasting furnace while passing air through the material. The atomic ratio of V:Cr:B:P in the catalyst was 1:1:0.5:0.015. The amount of catalyst held on silica was 50%. The catalyst had a spherical form. The particle size of the resulting catalyst was 20–150 μm. The bulk density of the catalyst was 0.95 g/ml.

The catalyst (40 ml) was charged into a stainless steel reactor having an inside diameter of 21 mm heated by molten salt. A gaseous mixture of 1.4% by volume of 3-methylpyridine, 5.2% by volume of ammonia and 93.5% by volume of air was passed through the fluidized bed catalyst at 375° C. and SV of 800 hour$^{-1}$. Gas chromatograph analysis showed that the conversion of 3-methylpyridine was 95.0% and that the yield of 4-cyanopyridine was 88%.

EXAMPLE 4

A gaseous mixture of 1.4% by volume of 4-methylpyridine, 3.5% by volume of ammonia and 95% by volume of air was passed through the catalyst of Example 3 at 350° C. by using the reactor of Example 3 and SV of 700 hour$^{-1}$. Gas chromatograph analysis showed that the conversion of 4-methylpyridine was 100% and that the yield of 4-cyanopyridine was 93%.

EXAMPLE 5

The catalyst (6 l) of Example 3 was charged into a stainless steel reactor having an inside diameter of 80 mm heated by molten salt.

A gaseous mixture of 3.0% by volume of 3-methylpyridine, 10.5% by volume of ammonia and 86.5% by volume of air was passed through the catalyst at 385° C. and SV of 600 hour$^{-1}$. Gas chromatograph analysis showed that the conversion of 3-methylpyridine was 100% and that the yield of 3-cyanopyridine was 91%.

EXAMPLE 6

A 500 ml of water was added to 229 g of vanadium pentaoxide $V_2O_5$, followed by heating to 80°–90° C. Then 477 g of oxalic acid $(COOH)_2 2H_2O$ was gradually added with well stirring to obtain a vanadyl oxalate solution. Separately, 400 ml of water was added to 963 g of oxalic acid, followed by heating to 50°–60° C. Then a solution of 252 g of chromic anhydride $CrO_3$ in 200 ml of water was gradually added to the oxalic acid solution with well stirring to obtain a chromium oxalate solution.

The resulting chromium oxalate solution was mixed drop-wise with the resulting vanadyl oxalate solution at 50°–60° C. to prepare a vanadium-chromium solution. To this solution was added drop-wise a solution of 44 grams of ammonium paramolybdate $(NH_4)_6Mo_7O_{24}4H_2O$ in 300 ml of water and furthermore, 1667 g of a 30 wt % aqueous silica sol.

To this slurry was added 78 g of boric acid $H_3BO_3$, then this slurry was well mixed and concentrated until amount of the liquid reached about 3800 g.

This catalyst solution was spray-dried with an inlet gas temperature of 250° C. and an outlet temperature of 130° C. The thus spray-dried catalyst was dried in a drier of 130° C. for 12 hours. Then, the catalyst was preliminary calcined at 400° C. for 1 hour and thereafter calcined at 550° C. for 8 hours while passing air. This catalyst had an atomic ratio V:Cr:Mo:B of 1:1:0.1:0.5 and an oxide concentration of 50 wt %.

A portion of the catalyst (6 l) was charged into a stainless steel reactor having an inside diameter of 80 mm and heated by molten salt. A gaseous mixture of 3.0% by volume of 3-methylpyridine, 12.0% by volume of ammonia and 85% by volume of air was passed through the fluidized bed catalyst at 390° C. and SV of 600 hour$^{-1}$. The gas chromatograph analysis showed that the conversion of 3-methylpyridine was 99% and that the yield of 3-cyanopyridine was 93%.

EXAMPLE 7

A gaseous mixture of 3.0% by volume of 4-methylpyridine, 10.0% by volume of ammonia and 87.0% by volume of air was passed through the catalyst of Example 6 at 360° C. and SV of 600 hour$^{-1}$. The gas chromatograph analysis showed that the conversion of 4-methylpyridine was 100% and that the yield of 4-cyanopyridine was 95%.

When cyanopyridines are prepared according to the present invention, the conversion of methylpyridines as a raw material is strikingly high and the yield of cyanopyridines is also high, as is apparent from the working examples.

It is unnecessary to add a large volume of steam to the reaction system, when carrying out the present process. Cyanopyridines can thus be effectively prepared by using a fluidized bed catalyst.

What is claimed is:

1. A process for producing a cyanopyridine comprising, reacting a corresponding methylpyridine, ammonia and an oxygen-containing gas in the presence of a composition selected from the group consisting of:
   (a) a catalyst consisting essentially of a vanadium oxide, a chromium oxide, a boron oxide and a phosphorus oxide, wherein the atomic ratio of vanadium, chromium, boron and phosphorous in said catalyst is 1:0.5 to 2:0.2 to 1.2:0 to 0.3, and
   (b) a catalyst consisting essentially of a vanadium oxide, a chromium oxide, a molybdenum oxide and a boron oxide, wherein the atomic ratio of vanadium, chromium, molybdenum and boron in said catalyst is 1:0.5 to 2:0.01 to 1.2:0.01 to 1.2.

2. The process of claim 1 wherein the reaction is carried out at a temperature of 300°–500° C.

3. The process of claim 1 wherein the ammonia is used in amount of 2–10 times the theoretical amount.

4. The process of claim 1 wherein the oxygen is used in amount of 2–50 times the theoretical amount.

5. The process of claim 1 wherein the reaction is carried out in a fluidized bed catalyst.

* * * * *